United States Patent [19]
Ray et al.

[11] Patent Number: 5,529,999
[45] Date of Patent: Jun. 25, 1996

[54] ANTITUMOR COMPOSITIONS AND METHODS OF TREATMENT

[75] Inventors: James E. Ray; John E. Toth, both of Indianapolis, Ind.

[73] Assignee: Eli Lilly and Company, Indianapolis, Ind.

[21] Appl. No.: 206,806

[22] Filed: Mar. 4, 1994

[51] Int. Cl.⁶ ............... A61K 31/495; C07D 405/12; C07D 403/12; C07D 241/44
[52] U.S. Cl. ............ 514/249; 544/354; 544/356; 548/551; 549/466
[58] Field of Search ............... 544/356; 514/249

[56] References Cited

U.S. PATENT DOCUMENTS

| | | | |
|---|---|---|---|
| 4,845,128 | 7/1989 | Harper et al. | 514/592 |
| 4,931,433 | 6/1990 | Tolman | 514/157 |
| 5,110,830 | 5/1992 | Harper et al. | 514/592 |
| 5,116,874 | 5/1992 | Poore | 514/592 |
| 5,169,860 | 12/1992 | Mohamadi et al. | 514/415 |
| 5,254,582 | 10/1993 | Boder et al. | 514/469 |
| 5,260,338 | 11/1993 | Harper et al. | 514/592 |
| 5,262,440 | 11/1993 | Ehlhardt et al. | 514/392 |

OTHER PUBLICATIONS

Branda et al., *Biochemical Pharmacology* 37 pp. 4557–4564 (1988).
Advanced Organic Chemistry (3rd Ed.) by Jerry March, pp. 445, 475, 550–551, 637, 648, 1087. (1985).
Howbert et al., *J. Med. Chem.* vol. 33, pp. 2393–2407 (1990).

*Primary Examiner*—Emily Bernhardt
*Attorney, Agent, or Firm*—Robert D. Titus; Paul J. Gaylo; David E. Boone

[57] ABSTRACT

This invention provides certain sulfonamidoquinoxaline derivatives and methods for using them in the treatment of susceptible neoplasms in mammals. Also provided are certain novel pharmaceutical formulations employing these sulfonamidoquinoxaline derivatives, in combination with a carrier, diluent or excipient.

15 Claims, No Drawings

ANTITUMOR COMPOSITIONS AND METHODS OF TREATMENT

BACKGROUND OF THE INVENTION

In recent years fundamental advances have been made in the development of chemical agents and regimens of therapy to combat neoplastic diseases. Despite these continuing advances, cancers continue to exact intolerable levels of human pain and suffering. The need for new and better methods of treating neoplasms and leukemias continues to fuel efforts to find new classes of antitumor compounds, especially in the area of inoperable or metastatic solid tumors, such as the various forms of lung cancer. Of the one million new cases of cancer diagnosed in the United States each year, more than 90% represent non-hematopoetic tumors, where improvements in five-year survival rates have been modest, at best. B. E. Henderson, et al,, *Science*, 254:1131–1137 (1991).

The recent avalanche of information regarding the basic biological processes involved in neoplasms has led to a deeper understanding of the heterogeneity of tumors. Ongoing work has led to the realization that individual tumors may contain many subpopulations of neoplastic cells that differ in crucial characteristics such as karyotype, morphology, immunogenicity, growth rate, capacity to metastasize, and response to antineoplastic agents.

It is because of this extreme heterogeneity among populations of neoplastic cells that new chemotherapeutic agents should have a wide spectrum of activity and a large therapeutic index. In addition, such agents must be chemically stable and compatible with other agents. It is also important that any chemotherapeutic regimen be as convenient and painless as possible to the patient.

This invention reports a series of novel sulfonamidoquinoxalines that are useful in the treatment of solid tumors. The compounds and their formulations are novel.

One sulfonamidoquinoxaline, 4-amino-N-(5-chloro-2-quinoxalinyl)benzenesulfonamide (also known as chloroquinoxaline sulfonamide, CQS, and CSQ), is currently in clinical trials as an antitumor agent. J. S. Fisherman, et al., *Investigational New Drugs*, 11:1–9 (1993); U.S. Pat. No. 4,931,433, issued Jun. 5, 1990.

The sulfonamidoquinoxalines of the instant invention are structurally related to diarylsulfonylureas which are useful as antitumor agents. e.g., U.S. Pat. No. 5,169,860, of F. Mohamadi and M. Spees, issued Dec. 8, 1992; U.S. Pat. No. 4,845,128 of Harper, et al,, issued Jul. 4, 1989; U.S. Pat. No. 5,110,830 of Harper, et al., issued May 5, 1992; U.S. Pat. No. 5,116,874 of G. A. Poore, issued May 26, 1992; European Patent Publication 0467613 (published. Jan. 22, 1992); Grindey,. et al., *American Association of Cancer Research*, 27:277 (1986); and Houghton, et al., *Cancer Chemotherapy and Pharmacology*, 25:84–88 (1989).

SUMMARY OF THE INVENTION

This invention provides a method of treating a susceptible neoplasm in a mammal which comprises administering to a mammal in need of said treatment an effective amount for treating a susceptible neoplasm of a compound of Formula I:

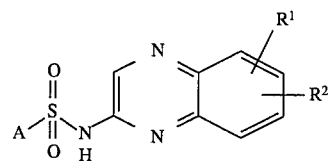

wherein:
A is phenyl, naphthyl, heterocyclic, or unsaturated heterocyclic,
    said groups being optionally substituted with one or more halo, trifluoromethyl, $C_1$–$C_6$ alkyl, or —$NR^3R^4$,
    where $R^3$ and $R^4$ are independently selected from the group consisting of hydrogen and $C_1$–$C_6$ alkyl;
$R^1$ and $R^2$ are independently selected from the group consisting of hydrogen, trifluoromethyl, halo, and $C_1$–$C_6$ alkyl, provided that $R^1$ and $R^2$ cannot both be hydrogen; provided that when one of $R^1$ and $R^2$ is hydrogen and the other is halo, $R^3$ and $R^4$ cannot both be hydrogen; or a tautomer or pharmaceutically acceptable salt or solvate thereof.

This invention also provides the novel compounds of Formula I and the salts and solvates thereof as well as pharmaceutical formulations comprising an effective amount of a compound of Formula I, or a pharmaceutically acceptable salt or solvate thereof, in combination with a suitable pharmaceutical carrier, diluent, or excipient.

DETAILED DESCRIPTION AND PREFERRED EMBODIMENTS

The terms and abbreviations used in the instant examples have their normal meanings unless otherwise designated. For example "°C" refers to degrees Celsius; "N" refers to normal or normality; "mmol" refers to millimole or millimoles; "g" refers to gram or grams; "ml" means milliliter or milliliters; "M" refers to molar or molarity; "FDMS" refers to field desorption mass spectrometry; "IR" refers to infrared spectroscopy; and "NMR" refers to nuclear magnetic resonance spectroscopy.

As used herein, the term "halo" refers to fluoro, chloro, bromo, and iodo.

The term "$C_1$–$C_6$ alkyl" refers to straight and branched chains of 1 to 6 carbon atoms and includes, but is not limited to, methyl, ethyl, propyl, isopropyl, butyl, isobutyl, t-butyl, pentyl, isopentyl, and hexyl.

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quarternized and including a bicyclic group in which any of the above-defined heterocyclic rings is fused to a benzene ring. The unsaturated heterocyclic ring may be attached at any heteroatom or carbon atom which affords a stable structure.

Examples of such heterocycles and unsaturated heterocycles include piperidinyl, piperazinyl, hexamethyleneiminyl, heptamethyleneiminyl, pyrrolyl, 4-piperidonyl, pyrrolidinyl, pyrazolyl, pyrazolidinyl, imidazolyl, imidazolinyl, imidazolidinyl, pyridyl, pyrazinyl, benzodioxinyl, benzodioxolyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, tetrahydronaphthyl, indolyl, quinolinyl, isoquinolinyl, benzimidazolyl, thiadiazolyl, benzopyranyl, benzothiazolyl, furyl, tetrahydrofuryl, tetrahydropyranyl, thienyl, benzothienyl, thiamorpholinyl, thiamorpholinyl-sulfoxide, thiamorpholinylsulfone, oxadiazolyl, triazolyl, tetrahydroquinolinyl, tetrahydrisoquinolinyl, benzofuryl, indolinyl, 2,3-dihydrobenzofuryl, indenyl, and indanyl.

The compounds of the present invention are derivatives of quinoxaline which are named and numbered according to the Ring Index, The American Chemical Society, as follows.

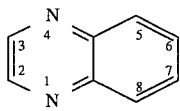

The preferred compounds employed in the methods of this invention and the preferred compounds of this invention are those compounds of Formula I in which:

(i) $R^1$ and $R^2$ are independently selected from the group consisting of hydrogen, chloro, fluoro, bromo, iodo, methyl, ethyl, and trifluoromethyl; and (ii) A is substituted phenyl, naphthyl, benzofuryl, 2,3-dihydrobenzofuryl, benzothienyl, indolyl, indolinyl, N-substituted indolyl, N-substituted indolinyl, indanyl, or indenyl.

The compounds of Formula I can be prepared by methods known in the literature. See, e.g., F. J. Wolf, et al., *Journal of the American Chemical Society*, 71:6 (1949). Generally, these methods involve the reaction of a sulfonamide of Formula II

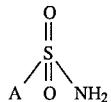

with an appropriately substituted quinoxaline of Formula III

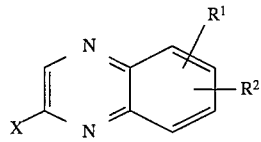

where X is halo. This reaction is generally performed in a non-reactive solvent at temperatures ranging from about −15° C. to about 80° C. Preferred solvents are polar aprotic solvents such as N,N-dimethylformamide, N,N'-dimethylpropyleneurea, dimethylacetamide, and dimethylsulfoxide. It is especially preferred to perform this reaction at temperatures of from about 15° C. to about 60° C. The product thus obtained can be purified, if desired, by any of a number of methods known to those skilled in the art, such as chromatography or crystallization.

In an alternative process a sulfonyl halide of Formula IV

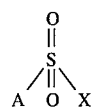

may be reacted with an amino-substituted quinoxaline of Formula V.

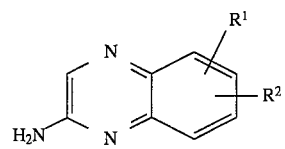

This reaction is performed in pyridine or in an inert solvent such as methylene chloride, with at least one equivalent of a tertiary amine or pyridine base.

The intermediates of Formulas II and IV can be prepared by methods known in the art. For example, the compound of Formula II which is 2,3-dihydrobenzofuran-5-sulfonamide or the compound of Formula IV which is 2,3-dihydrobenzofuran-5-sulfonyl chloride may be prepared by the methods described in U.S. Pat. No. 5,254,582, issued Oct. 19, 1993. The compounds of Formula II in which A is benzofuryl, benzothienyl, or indolyl may be prepared by the methods taught in U.S. Pat. No. 5,169,860, issued Dec. 8, 1992. Those compounds of Formula II in which A is substituted phenyl may be prepared as described in U.S. Pat. No. 4,845,128, issued Jul. 4, 1989, U.S. Pat. No. 5,110,830, issued May 5, 1992, and U.S. Pat. No. 5,260,338, issued Nov. 9, 1993. Those compounds of Formula II in which A is N-substituted indolinyl, indanyl, benzodioxinyl, benzodioxolyl, or tetrahydronaphthyl may be prepared by the teachings of U.S. Pat. No. 5,116,874, issued May 26, 1992. Those compounds of Formula II in which A is indenyl may be synthesized as taught in U.S. Pat. No. 5,262,440, issued Nov. 16, 1993. All of the aforementioned United States patents are herein incorporated by reference.

The compounds of Formula III may be prepared by methods taught in the literature such as by the condensation of a substituted o-phenylenediamine of Formula VI

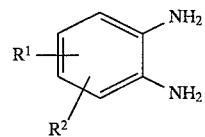

with a glyoxylic acid solvate, such as glyoxylic acid monohydrate, or derivative such as butyl glyoxalate to give a 2-hydroxyquinoxaline, which is then halogenated to give the substituted 2-haloquinoxaline of Formula III. The necessary diamines may be purchased from commercial sources or may be prepared by the reduction of the corresponding substituted nitroaniline or dinitrobenzene, usually by stannic chloride/concentrated hydrochloric acid reduction. The chlorination of the hydroxy compounds is achieved by treatment with phosphorous chlorides, most preferably with phosphorous pentachloride or phosphorous oxychloride.

The condensation reaction is performed at temperatures ranging from about 15° C. to the reflux temperature of the solvent employed. The chlorination reaction is usually performed at the reflux temperature of the phosphorous oxychloride. The regioisomeric 2-haloquinoxalines produced by the application of this method to non-symmetrically substituted o-phenylenediamines are separated using well-known techniques, such as silica gel chromatography or crystallization.

In an alternative process of producing the 2-hydroxyquinoxaline described supra, the substituted o-phenylenediamine of Formula VI is first reacted with a 2-haloacetamide as described in R. W. Holley, et al., *Journal of the American Chemical Society*, 74:3069 (1952) to produce a substituted 1,2,3,4-tetrahydro-2-quinoxalinone of Formula VII.

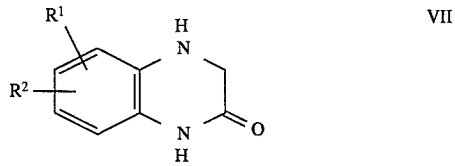

This reaction is performed in a non-reactive polar solvent such as water, methanol, or ethanol. The 1,2,3,4-tetrahydro-2-quinoxalinone is then oxidized to produce a substituted 2-hydroxyquinoxaline. The oxidation is performed using techniques well known in the scientific literature. See, e.g., R. L. Wear, et al., *Journal of the American Chemical Society*, 72:2893 (1950). This oxidation is usually performed using a peroxide, especially hydrogen peroxide, in the presence of a base. Preferred bases include inorganic bases, such as ammonium or alkali or alkaline earth metal hydroxides, carbonates, bicarbonates, and the like. Especially preferred bases for this purpose include sodium hydroxide, lithium hydroxide, and potassium hydroxide.

As noted supra, this invention includes the pharmaceutically acceptable salts of the compounds defined by Formula I. A compound of this invention can possess a sufficiently acidic functional group, and accordingly react with any one a number of organic and inorganic bases to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable organic or inorganic base. Such salts are known as base addition salts.

Base addition salts include those derived from inorganic bases, such as ammonium or alkali or alkaline earth metal hydroxides, carbonates, bicarbonates, and the like. Such, bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. Especially preferred organic base salts employ primary, secondary, and tertiary alkyl amines such as methylamine, triethylamine, N-methyl-D-glucamine, and the like.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solvates of the compounds of Formulas I. Many of the Formula I compounds can combine with solvents such as water, methanol, ethanol and acetonitrile to form pharmaceutically acceptable solvates such as the corresponding hydrate, methanolate, ethanolate and acetonitrilate.

Within the present invention it is to be understood that the quinoxaline of Formula I may exhibit the phenomenom of tautomerism and that the formula drawings presented within this specification may represent only one of the possible tautomeric forms. The present invention, however, encompasses any tautomeric form of the compounds of Formula I and is not to be limited to any one tautomeric form depicted in the drawings.

The following examples further illustrate the preparation of the compounds of Formula I. These examples are illustrative only and are not intended to limit the scope of the invention in any way.

EXAMPLE 1

Preparation of 4-N',N'-dimethylamino-N-(6,7-dichloro-2-quinoxalinyl)benzenesulfonamide A suspension of sodium hydride (60%, 160 mg, 4.0 mmol) in N,N-dimethylformamide (10 ml) under a nitrogen atmosphere at room temperature was treated with p-dimethylaminobenzenesulfonamide (300 mg, 1.5 mmol), and after stirring one hour, solid 2,6,7-trichloroquinoxaline (308 mg, 1.33 mmol) was added. After five hours, additional 2,6,7-trichloroquinoxaline (45 mg, 0.20 mmol) was added and stirring continued overnight. The reaction mixture was carefully poured into excess pH 4.0 buffer and extracted with ethyl acetate (3X). The combined extract was washed with water, brine and dried over sodium sulfate. Filtration and evaporation yielded a solid which was purified by silica gel flash chromatography (EtOAc/hexanes) to yield the title product (100 mg, 19%) as a solid.

Analysis of the title compound gave the following results: $^1$H NMR (300 MHz, $d_6$-DMSO)$\delta$2.94(s, 6H, CH$_3$), 6.74, (d, 2H, J=9.1 Hz, Ar-H), 7.87 d, 2H, J=9.0 Hz, Ar-H), 8.07 (s, 1H, Ar-H), 8.20 (s, 1H, Ar-H), 8.52 (s, 1H, Ar-H), 11.82 (s, 1H, exchanges with D$_2$O, NH); IR(KBr) 3114, 3057, 1601, 1383, 1316 and 1154 cm$^{-1}$; UV(EtOH)$\lambda$max($\epsilon$) 216.0(41035), 254.4(29214), 283.2(23127) and 350.2 (8436) nm; FDMS(DMSO) m/e=396, 398, 400 (M$^+$).

Analysis of $C_{16}H_{14}Cl_2N_4O_2S$:

Theory: C, 48.37; H, 3.55; N, 14.10.

Found: C, 48.16; H, 3.56; N, 13.92.

Preparation 1

Preparation of 2,5- and 2,8-Dichloroquinoxalines

These compounds were prepared using techniques well known in the art. See, e.g., L. McQuaid, et al., *Journal of Medicinal Chemistry*, 35:3319 (1992); F. J. Wolf, et al., *Journal of the American Chemical Society*, 71:6 (1949); U.S. Pat. No. 5,153,196, issued Oct. 6, 1992; and U.S. Pat. No. 5,196,421, issued Mar. 23, 1993, all of which are herein incorporated by reference. In the protocol employed 1,2-diamino-3-chlorobenzene was converted to a mixture of 2,5- and 2,8-dichloroquinoxalines by condensing with glyoxalic acid hydrate to give a mixture of 5- and 8-chloro-2-hydroxyquinoxaline which was then chlorinated. These two dichloroquinoxalines were separated by silica gel flash chromatography (EtOAc/hexanes).

Analysis of the compounds gave the following results:

2,5-dichloroquinoxaline : mp=137°–138.5° C.; $^1$H NMR (300 MHz, $d_6$-DMSO)$\delta$7.88 (t, 1H, J=8.1 Hz, Ar-H), 8.01(d, 1H, J=8.1 Hz, Ar-H), 8.06(d, 1H, J=8.1 Hz, Ar-H), 9.08(s, 1H, Ar-H); FDMS (DMSO) m/e=198, 200,202 (M$^+$).

Analysis of $C_8H_4Cl_2N_2$:

Theory: C, 48.28; H, 2.03; N, 14.07.

Found: C, 48.24; H, 2.23; N, 13.92.

2,8-dichloroquinoxaline: mp=120°–122° C.; $^1$H NMR (300 MHz, $d_6$-DMSO)δ7.87 (t, 1H, J=8.1 Hz, Ar-H) , 8.12 ( overlapping d, 2H, Ar-H), 9.07 (s, 1H, Ar-H) ; FDMS (DMSO) m/e=198, 200, 202 (M$^+$).

Analysis of $C_8H_4Cl_2N_2$:
Theory: C, 48.28; H, 2.03; N, 14.07.
Found: C, 48.46; H, 2.21; N, 13.80.

EXAMPLE 2

Preparation of 4-N',N'-dimethylamino-N-(5-chloro-2-quinoxalinyl)benzenesulfonamide A suspension of sodium hydride (60%, 114 mg, 2.85 mmol) in N,N-dimethylformamide (10 ml ) under nitrogen at room temperature was treated with p-dimethylaminobenzenesulfonamide (214 mg, 1.07 mmol), and after stirring one hour, solid 2,5-dichloroquinoxaline (231 mg, 1.16 mmol) was added. After stirring overnight, the reaction mixture was poured into water (100 ml) and the pH adjusted to 3–4 by the addition of 1N hydrochloric acid solution. The resulting precipitate was collected, dried and purified by silica gel flash chromatography (EtOAc/hexanes/THF) to yield the title product (56 mg, 14%) as a solid.

Analysis of the title compound gave the following results: $^1$H NMR (300 MHz, $d_6$-DMSO)δ2.92(s, 6H, $CH_3$), 6.72 (d, 2H, J=7.8 Hz, Ar-H), 7.68–7.84 (overlapping multiplets, 3H, Ar-H), 7.85 (d, 2H, J=8.0 Hz, Ar-H), 8.61 ( s, 1H, Ar-H), 11.78(s, 1H, exchanges with $D_2O$, NH); IR(KBr) 1600, 1582, 3.448, 1148 and 1089 cm$^{-1}$; FDMS(DMSO) m/e=362, 364 (M$^+$).

Analysis of $C_{16}H_{15}ClN_4O_2S$:
Theory: C, 52.96; H, 4.17; N, 15.44.
Found: C, 53.17; H, 4.30; N, 15.30.

Preparation 2

Synthesis of N-methylindoline-5-sulfonamide

A 3-liter, 3-neck flask with mechanical stirrer and nitrogen purge line was charged with ethyl-indoline-1-carboxylate-5-sulfonamide (27 g, 100 mmol), as prepared in Example 2, and 1000 ml of anhydrous tetrahydrofuran. Under nitrogen purge was then added lithium aluminum hydride (95%, 10 g, 250 mmol) in portions over 20 minutes, resulting in strong exotherms. The reaction was stirred at room temperature and monitored using HPLC (reverse-phase, 40/60/0.2% acetonitrile/water/phosphoric acid, 1 ml/min, monitoring at 254 nm). After 2 hours the mixture was cooled in an ice-bath and carefully quenched by the addition of ice until no further reaction was noted. Concentrated hydrochloric acid (65 ml) was next added until the pH equaled 3. The inorganic solids were removed by filtration and the filtrate evaporated to give a tan solid (23 g). Purification was effected by slurrying the crude solid in 250 ml of $H_2O$ for 30 minutes and filtering, followed by rinsing of the cake with $H_2O$ (300 ml) and diethyl ether (300 ml). Vacuum drying gave 17.3 g (81%) of the product sulfonamide. Recrystallization from methanol gave an analytical sample.

Analysis of the product gave the following results: mp=176°–177° C.; $R_f$(1/1 EtOAc/hexane)=0.29; $^1$H NMR (300 MHz, $d_6$-DMSO)δ2.74 (s 3H, $NCH_3$), 2.92 (t, 2H, J=8.4 Hz, $CH_2CH_2$), 3.38 (t, 2H, J=8.4 Hz, $CH_2CH_2$), 6.47 (d, 1H, J=8.3 Hz, Ar-H), 6.91 (bs, 2H, exchanges with $D_2O$ $SO_2NH_2$), 7.39 (s, 1H, Ar-H) and 7.44 (d, 1H, J=8.3 Hz, Ar-H); IR(KBr)3314, 3239, 1605, 1509, 1313, 1170 and 1062 cm$^{-1}$; FDMS(MeOH) m/e 212 (M$^+$).

Analysis for $C_9H_{12}N_2O_2S$:
Theory: C, 50.92; H, 5.70; N, 13.20.
Found: C, 50.87; H, 5.62; N, 12.91.

EXAMPLE 3

Preparation of N-(5-chloro-2-quinoxalinyl)-2,3-dihydro-1-methyl-1H-indole-5-sulfonamide In a manner similar to Example 2, N-methylindoline-5-sulfonamide (212 mg, 1.0 mmol) prepared as described in Preparation 2, supra, sodium hydride (60%, 215 mg, 5.4 mmol) and 2,5-dichloroquinoxaline, after six hours at room temperature yielded a crude solid that was purified by silica gel radial chromatography (2 mm, $CH_2Cl_2$/MeOH followed by 2 mm, EtOAc/hexanes) to provide the title product (40 mg, 11%) as a solid.

Analysis of the title compound gave the following results: $^1$H NMR (300 MHz, $d_6$-DMSO) δ2.73(s, 3H, $CH_3$), 2.92(t, 2H, J=8.5 Hz, $CH_2$), 3.40 t, 2H, J=8.5 Hz, $CH_2$), 6.45(d, 1H, J=8.4 Hz, Ar-H), 7.61–7.78(overlapping multiplets, 5H, Ar-H), 8.61(s, 1H, Ar-H), 11.71(s, 1H, exchanges with $D_2O$, NH); IR(KBr) 1606, 1580, 1449, 1280 and 1132 cm$^{-1}$; FDMS(DMSO) m/e=374, 376 (M$^+$).

Analysis of $C_{17}H_{15}ClN_4O_2S$:
Theory: C, 54.47; H, 4.03; N, 14.95.
Found: C, 54.47; H, 4.08; N, 14.73.

Preparation 3

Synthesis of 2,3-dihydrobenzofuran-5-sulfonamide

This compound was prepared essentially according to the teachings of J. A. Aikins, et al., European Patent Publication 254,577, published Jan. 27, 1988. N,N-dimethylformamide (23.0 ml, 297 mmol) was cooled in an ice-salt bath and treated dropwise with sulfuryl chloride (20.0 g, 148 mmol) at such a rate that the reaction temperature was maintained below 15° C. To this was added 2,3-dihydrobenzofuran (17.0 g, 142 mmol), and after warming to room temperature, the reaction mixture was rapidly heated to 130° C. over ten minutes, and then allowed to cool to room temperature. The reaction mixture was poured into water/ice/dichloromethane, 1/5/1 (700 ml), and the organic layer collected. The aqueous layer was diluted with water (100 ml) and extracted with dichloromethane. The combined organic phase was dripped into an ammonium hydroxide solution (3N, 250 ml), and allowed to stir overnight. Residual dichloromethane was removed by distillation and the resulting solid collected on a filter, washed with a small amount of water, followed by ether and then dried by aspiration to provide 12.8 g (45%) of the product.

Analysis of the product gave the following results: mp=163°–164.5° C.; $^1$H NMR (300 MHz, $d_6$-DMSO) δ3.21 (t, 2H, J=8.8 Hz, $CH_2$), 4.60 (t, 2H, J=8.8 Hz, $CH_2$), 6.86 (d, 1H, J=8.4 Hz, Ar-H), 7.12 (bs, 2H, exchanges with $D_2O$, $SO_2NH_2$), 7.56 (d, 1H, J=8.4 Hz, Ar-H), 7.64 (s, 1H, Ar-H); IR(KBr) 3356, 3255, 1606, 1590, 1557, 1407, 1442, 1314, 1249, 1149, 1116, 1070, 982, 923 and 836 cm$^{-1}$; FDMS (MeOH) m/e 200 (M$^+$+1).

Analysis for $C_8H_9NO_3S$:
Theory: C, 48.23; H, 4.55; N, 7.03; S, 16.09.
Found: C, 48.01; H, 4.71; N, 7.00; S, 16.36.

Preparation 4

Alternative Synthesis of 2,3-dihydrobenzofuran-5-sulfonamide

Into a 250 ml, 3-necked flask under nitrogen purge were added sulfur trioxide-N,N-dimethylformamide complex (9.2 g, 60 mmol) and 1,2-dichloroethane (20 ml). The slurry was stirred at room temperature and 2,3-dihydrobenzofuran (6.0 g, 50 mmol) was added dropwise at room temperature. The purple slurry was slowly heated to 85° C. over the course of one hour. The progress of the reaction was monitored using thin layer chromatography.

Once the reaction was completed, the reaction mixture was allowed to cool to room temperature and thionyl chloride (7,.2 g, 60 mmol) was added dropwise. The reaction mixture was slowly heated to 75° C. and maintained at that temperature until the reaction, as determined by thin layer chromatography, had completed.

The reaction mixture was allowed to cool to room temperature and water (100 ml) was added. The aqueous layer was collected and extracted with 1,2-dichloroethane (3×25 ml). The combined 1,2-dichloroethane layers were washed with water (25 ml) and dried over magnesium sulfate. The magnesium sulfate was filtered and washed with 1,2-dichloroethane.

This 1,2-dichloroethane solution containing the desired sulfonyl chloride was added to a solution of 1,2-dichloroethane (20 ml) and gaseous ammonia (14.7 g) which was cooled by a dry ice/acetone bath. This reaction was allowed to stir overnight, eventually coming to room temperature.

The precipitate was filtered and washed with 1,2-dichloroethane, followed by a wash with water and, finally, a wash with ether. The precipitate was vacuum dried to give 6.9 g of the title product (Sample A). The 1,2-dichloroethane filtrate was evaporated under vacuum to give 2.0 g of solid which was slurried with 25 ml of water. This precipitate was filtered and washed with water and ether, the ether being removed by vacuum-drying. The 1.2 g of solid title compound recovered by this extraction of the filtrate (Sample B), when combined with the 6.9 g of title compound in the earlier precipitate, results in an overall 81% yield of the title compound. Nuclear magnetic resonance assays confirmed the identity of the title compound.

Analysis for $C_8H_9NO_3S$:

Sample A

FDMS (MeOH) m/e 199 (M$^+$).

Theory: C, 48,23; H, 4.55; N, 7.03.

Found: C, 48.33; H, 4.47; N, 6.96.

Sample B

FDMS (MeOH) m/e 199 (M$^+$).

Theory: C, 48,23; H, 4.55; N, 7.03.

Found: C, 48.33; H, 4.49; N, 7.01.

EXAMPLE 4

Preparation of N-(5-chloro-2-quinoxalinyl)-2,3-dihydrobenzofuran-5-sulfonamide In a manner similar to Example 2, 2,3-dihydrobenzofuran-5-sulfonamide (400 mg, 2.01 mmol), sodium hydride (60%, 315 mg, 7.9 mmol) and 2,5-dichloroquinoxaline (600 mg, 3.0 mmol) were reacted at room temperature for 24 hours. The reaction mixture was heated to 55° C. for thirty min, cooled to room temperature and poured into water. Acidification with 1N hydrochloric acid solution yielded a precipitate which was collected and dried. This precipitate was washed with methylene chloride and the solid obtained by evaporation of the filtrate was purified by silica gel flash chromatography (ether/hexanes). The resulting foam was broken up in hexanes, collected and dried, finally under vacuum at 80° C. to yield the title product (85 mg, 12%) as a solid.

Analysis of the title compound gave the following results: $^1$H NMR (300 MHz, $d_6$-DMSO) δ 3.21(t, 2H, J=8.8 Hz, CH$_2$), 4.58 (t, 2H, J=8.8 Hz, CH$_2$), 6.89(d, 1H, J=8.4 Hz, Ar-H), 7.66–7.81 (overlapping multiplets,3H, Ar-H), 7.89(d, 1H, J=8.4 Hz, Ar-H), 7.94(s, 1H, Ar-H), 8.63 (s, 1H, Ar-H), 11.97 (s, 1H, exchanges with D$_2$O, NH); IR(KBr) 1617, 1583, 1485, 1241 and 1148 cm$^{-1}$; FDMS(DMSO) m/e=361, 363 (M$^+$).

Analysis of $C_{16}H_{12}ClN_3O_3S$:

Theory: C, 53.12; H, 3.34; N, 11.61.

Found: C, 52.86; H, 3.44; N, 11.37.

Preparation 5

Preparation of benzofuran-5-sulfonamide

A suspension of 2,3-dihydrobenzofuran-5-sulfonamide (19.9 g, 100 mmol) and 2,3-dichloro-5,6-dicyano-1,4-benzoquinone (DDQ) (56.7 g, 250 mmol) in dioxane (500 ml) was heated at reflux under nitrogen for 111 hours. The reaction mixture was reduced in volume by evaporation under vacuum and purified by silica gel flash chromatography (EtOAc/hexanes) to provide benzofuran-5-sulfonamide (3.5 g, 18% ) . This was combined with another lot of benzofuran-5-sulfonamide (1.0 g), slurried in ether, collected and vacuum dried at 45° C. overnight to give 4.5 g of benzofuran-5-sulfonamide.

Analysis of the compound gave the following results: $^1$H NMR (300 MHz, $d_6$-DMSO) δ 7.11 (d, 1H, J=1,7 Hz, Ar-H), 7.32 (s, 2H, exchanges with D$_2$O, NH); 7.73 (s, 2H, Ar-H), 8.14 (s, 2H, Ar-H); IR (KBr) 3345, 1537, 1456, 1321, 1260 and 1153 cm$^{-1}$; FDMS(DMSO) m/e=197(M$^+$).

Analysis of $C_8H_7NO_3S$:

Theory: C, 48.72; H, 3.58; N, 7.10.

Found: C, 48.66; H, 3.68; N, 7.17.

EXAMPLE 5

Preparation of N-(5-chloro-2-quinoxalinyl)benzofuran-5-sulfonamide

In a manner similar to Example 4, the reaction mixture from benzofuran-5-sulfonamide (397 mg, 2.01 mmol), sodium hydride (60%, 315 mg, 7.9 mmol) and 2,5-dichloroquinoxaline (600 mg, 3.01 mmol) was poured carefully into water and washed with hexanes. The hexane-free aqueous was acidified to a pH of 1–2 by the addition of 5N hydrochloric acid solution and the resulting precipitate was collected and dried. This precipitate was washed with methylene chloride and the solid obtained by evaporation of the filtrate was purified by radial silica gel chromatography (EtOAc/hexanes) followed by silica gel flash chromatography (diethyl ether/hexanes). The resulting foam which was broken up in hexanes, collected and dried, finally under vacuum at 80° C. to yield the title product (110 mg, 15%) as a solid.

Analysis of the title compound gave the following results: $^1$H NMR (300 MHz, d$_6$-DMSO) δ 7.15 (d, 1H, J=2.0 Hz, Ar-H), 7.64–8.0 (overlapping multuplets, 4H, Ar-H), 8.03 (d, 1H, J=7.3 Hz, Ar-H), 8.13 (d, 1H, J=2.0 Hz, Ar-H), 8.51 (s, 1H, Ar-H), 8.67 (s, 1H, Ar-H), 12.21 (s, 1H, exchanges with D$_2$O, NH); IR(KBr) 1617, 1581, 1453, 1263 and 1153 cm$^{-1}$; FDMS (DMSO) m/e=359, 361 (M$^+$).

Analysis of C$_{16}$H$_{10}$ClN$_3$O$_3$S:

Theory: C, 53.41; H, 2.80; N, 11.68.

Found: C, 52.95; H, 2.99; N, 11.47.

Preparation 6

Synthesis of 1-methyl-1H-indole-5-sulfonamide

N-methyl-indoline-5-sulfonamide (225 mg, 1.06 mmol), as prepared supra, was mixed with 10% palladium on carbon (84 mg) in methanol (8 ml) and these were refluxed for 23 hours. Additional 10% palladium on carbon (100 mg) and methanol (5 ml) were added, and refluxing continued for an additional 23 hours. The cooled reaction mixture was filtered through a Celite® pad, evaporated, and the crude solid redissolved in tetrahydrofuran and again filtered through a Celite® pad. Evaporation of the filtrate gave 211 mg (95%) of N-methyl-1H-indole-5-sulfonamide. This intermediate could also be produced from the reaction of N-methyl-indoline-5-sulfonamide and 2,3-dichloro-5,6-dicyano-1,4-benzoquinone (DDQ) in refluxing ethylene glycol monomethyl ether in 35% yield using known procedures. See, e.g. H. Breuer and H. Höhn, Chimie Therapeutique, 6:659 (1973).

Analysis of the product gave the following results: mp=225°–227° C.; Rf (EtOAc)=0.59; $^1$H NMR (300 MHz, d$_6$-DMSO) δ3.82 (s, 3H, N-CH$_3$), 6.58 (d, 1H, J=3.0 Hz, Ar-H), 7.11 (s, 2H, exchanges with D$_2$O, SO$_2$NH), 7.47 (d, 1H, J=3.0 Hz, Ar-H), 7.58 (s, 2H, Ar-H) and 8.03 (s, 1H, Ar-H); IR(KBr) 3330, 3235, 2948, 1512, 1326, 1145, and 1062 cm$^{-1}$; FDMS (MeOH) m/e 210 (M$^+$).

Analysis for C$_9$H$_{10}$N$_2$O$_2$S •0.33 THF:

Theory: C, 52.96; H, 5.44; N, 11.97.

Found: C, 52.62; H, 5.06; N, 11.53.

EXAMPLE 6

Preparation of N-(5-chloro-2-quinoxalinyl)-1-methyl-1H-indole-5-sulfonamide

In a manner similar to Example 2, 1-methyl-1H-indole-5-sulfonamide (373 mg, 1.78 mmol), prepared as described in Preparation 2, supra, sodium hydride (60%, 278 mg, 6.9 mmol) and 2,5-dichloroquinoxaline (530 mg, 2.66 mmol) were reacted at room temperature overnight. The reaction mixture was worked up as in Example 5 to yield, after radial silica gel chromatography (4 mm, EtOAc/hexanes) and vacuum drying at 80° C., the title product (280 mg, 42%) as a foam.

Analysis of the title compound gave the following results: $^1$H NMR (300 MHz, d$_6$-DMSO) d 3.77(s, 3H, CH$_3$), 6.65(d, 1H, J=2.8 Hz, Ar-H), 7.45(d, 1H, J=2.8 Hz, Ar-H), 7.57 (d, 1H, J=8.8 Hz, Ar-H), 7.63–7.79 (overlapping multuplets, 3H, Ar-H), 7.81(d, 1H, J=8.7 Hz, Ar-H), 8.40(s, 1H, Ar-H), 8.66(s, 1H, Ar-H), 11.93(s, 1H, exchanges with D$_2$O, NH); IR(KBr) 1581, 1492, 1449, 1316, 1282 and 1133 cm$^{-1}$; UV(EtOH) λ$_{max}$(ε) 208.5(40239), 232.5(50379), 256.0(26920) and 339.0(5749) nm; FDMS(DMSO) m/e= 372, 374 (M$^+$). Exact Mass (FAB): Theory CC$_{17}$H$_{13}$ClN$_4$O$_2$S+H$^+$: 373.0498. Found 373.0526.

Preparation 7

Preparation of 2,6- and 2,7-dichloroquinoxaline

In 1000 ml of water were combined 4-chloro-1,2-phenylenediamine (50 g, 0.34 mole) and 2-chloroacetamide (39 g, 0.41 mole) and the mixture heated at 100° C. with stirring for 3 hours. Filtration and vacuum drying gave 38.5 g (62%) of purple solid. NMR (300 MHz, d$_6$-DMSO) shows a 2:1 mixture of the regioisomeric 6- and 7-chloroquinoxalinones.

The quinoxalinone mixture (38.5 g, 0.21 mole) in a 3-neck round-bottom flask with mechanical stirrer was treated with 2N aqueous sodium hydroxide (530 ml, 1.06 mole) and 30% aqueous hydrogen peroxide (48 ml, 0.42 mole) and carefully heated on a steam bath. After the initial vigorous reaction subsided, the mixture was heated a further 2 hours. After cooling in an ice-bath, the reaction was neutralized by the addition of glacial acetic acid (100 ml). After stirring 20 minutes, the mixture was filtered, washed with water (500 ml) and vacuum dried to 27.5 g (73%) of the mixture of 6- and 7-chloro-2-hydroxyquinoxaline as a tan solid.

The mixture of hydroxyquinoxalines (36.3 g, 0.2 mole) was refluxed with phosphorous oxychloride (150 ml) for thirty minutes and poured onto ice. The resulting solid was rinsed with water (500 ml) and vacuum-dried to 37.7 g. Preparatory HPLC (silica gel, 100% hexanes to 2% EtOAc/hexanes) gave 3 fractions: 2,6-dichloroquinoxaline (3.8 g), 2,7-dichloroquinoxaline (8.3 g), and a mixed fraction (20 g).

Analysis of the compounds gave the following results:

2,6-dichloroquinoxaline: mp=156.5°–157° C.; $^1$H NMR (300 MHz, CDCl$_3$) δ7.77 (dd, 1H, J=2.3, 9.0 Hz, Ar-H), 7.98 (d, 1H, J=9.0 Hz, Ar-H), 8.13 (d, 1H, J=2.3 Hz, Ar-H), 8.80 (s 1H, Ar-H); IR(CHCl$_3$) 3008, 1606, 1549, 1481, 1270, 1151, 1094 and 902 cm$^{-1}$; UV(EtOH) λ$_{max}$(ε) 206.5 (33911), 242.5 (28052) and 328.5 (5867) nm; FDMS-(MeOH) m/e=198, 200, 202 (M$^+$).

Analysis of C$_8$H$_4$Cl$_2$N$_2$:

Theory: C, 48.28; H, 2.03; N, 14.07.

Found: C, 48.25; H, 2.02; N, 13.94.

2,7-dichloroquinoxaline: mp=142° C.; $^1$H NMR (300 MHz, CDCl$_3$) δ7.77 (dd, 1H, J=2.3, 9.0 Hz, Ar-H), 8.03 (d, 1H, J=2.3 Hz, Ar-H), 8.07 (d, 1H, J=9.0 Hz, Ar-H), 8.78 (s, 1H, Ar-H); IR(CHCl$_3$) 3008, 1606, 1550, 1482, 1241, 1107 and 964 cm$^{-1}$; UV(EtOH) λ$_{max}$(ε) 210.0 (29445), 242.5 (25208), 324.5 (6718) and 336.0 (5987) nm; FDMS(MeOH) m/e=198, 200, 202 (M$^+$).

Analysis of C$_8$H$_4$Cl$_2$N$_2$:

Theory: C, 48.28; H, 2.03; N, 14.07.

Found: C, 48.06; H, 2.03; N, 13.95.

EXAMPLE 7

Preparation of 4-N',N'-dimethylamino-N-(6-chloro-2-quinoxalinyl)benzenesulfonamide In a manner similar to Example 2, p-dimethylaminobenzenesulfonamide (1.8 g, 9.1 mmol), sodium hydride (60%, 1.46 g, 36.4 mmol) and 2,6-dichloroquinoxaline (2.0 g, 10 mmol) were reacted at 60° C. for 3 hours. The reaction mixture was worked up as in Example 2 to yield, after silica gel chromatography (EtOAc/hexanes/THF), 146 mg (4.4%) of the title product.

Analysis of the title compound gave the following results: mp=207°–208° C.; $^1$H NMR (300 MHz, d$_6$-DMSO) d 2.93(S, 6H, CH$_3$), 6.74(d, 2H, J=9.1 Hz, Ar-H), 7.78(m,2H, Ar-H), 7.85(d, 2H, J=9.1Hz, Ar-H), 7.98(s, 1H, Ar-H), 8.54(s, 1H, Ar-H), 11.67(s, 1H, exchanges with D$_2$O, NH); IR (KBr) 1603, 1354, 1312, 1163 and 1092 cm$^{-1}$; UV(EtOH) $\lambda_{max}(\epsilon)$ 206.0 (44457), 253.0 (30506), 282.5 (24808) and 348 (8444) nm; FDMS(DMSO) m/e=362, 364 (M$^+$).

Analysis of C$_{16}$H$_{15}$ClN$_4$O$_2$S:
Theory: C, 52.96; H, 4.17; N, 15.44.
Found: C, 53.14; H, 4.21; N, 15.31.

EXAMPLE 8

Preparation of
N-(6-chloro-2-quinoxalinyl)-2,3-dihydro-
1-methyl-1H-indole-5-sulfonamide In a manner similar to Example 2, N-methylindoline-5-sulfonamide (1.94 g, 9.1 mmol), sodium hydride (60%, 1.9 g, 48 mmol) and 2,6-dichloroquinoxaline (2.0 g, 10 mmol) were reacted for 2 hours at room temperature followed by 2 hours at 60° C. The reaction mixture was worked up as in Example 2 to give, after silica gel chromatography (EtOAc/hexanes/THF), the product, 345 mg (10.1%).

Analysis of the title compound gave the following results: mp=189°–190° C.; $^1$H NMR (300 MHz, d$_6$-DMSO) d 2.73(s, 3H, CH$_3$), 2.92(t, 2H, J=8.5 Hz, CH$_2$), 3.40(t, 2H, J=8.5 Hz, CH$_2$), 6.45(d, 1H, J=8.4 Hz, Ar-H), 7.60 (s, 1H, Ar-H), 7.70 (m, 3H, Ar-H),7.96(s, 1H, Ar-H), 8.54(s, 1H, Ar-H), 11.64 (s, 1H, exchanges with D$_2$O, NH); IR(KBr) 1607, 1458, 1349 and 1148cm$^{-1}$; UV(EtOH) $\lambda_{max}(\epsilon)$ 207.5 (47017), 227.0, (21534), 253.0 (26582), 291.5 (17627) and 348.0 (7137) nm; FDMS(DMSO) m/e=374, 376 (M$^+$).

Analysis of C$_{17}$H$_{15}$ClN$_4$O$_2$S:
Theory: C, 54.47; H, 4.03; N, 14.95.
Found: C, 54.23; H, 4.17; N, 15.03.

EXAMPLE 9

Preparation of
4-(N',N'-dimethylamino)-N-(7-chloro-2-
quinoxalinyl)benzenesulfonamide In a manner similar to Example 2, p-dimethylaminobenzenesulfonamide (2.3 g, 11.5 mmol), sodium hydride (60%, 1.9 g, 48 mmol) and 2,7-dichloroquinoxaline (2.3 g, 11.6 mmol) were reacted for 18 hours at room temperature followed by 20 minutes at 50° C. The reaction mixture was worked up as in Example 2 to give a solid which was dissolved in 150 ml water containing 8 ml of 1N sodium hydroxide and washed with diethyl ether (3×200 ml). After treatment with Norit A™, the solution was cooled in an ice-bath and acidified with glacial acetic acid. The resulting solid was collected by filtration, washed with water (100 ml) and vacuum dried to give the product as a yellow solid, 290 mg (6.9%). Recrystallization from toluene afforded an analytical sample.

Analysis of the title compound gave the following results: mp=206°–207° C.; $^1$H NMR (300 MHz, d$_6$-DMSO) δ2.93(s, 6H, CH$_3$), 6.74(d, 2H, J=9.1 Hz, Ar-H), 7.60(m,1H, Ar-H), 7.85(m overlapping d,, 4H, Ar-H), 8.51(s, 1H, Ar-H), 11.72(s, 1H, exchanges with D$_2$O, NH); IR(KBr) 1600, 1322, 1154 and 1094 cm$^{-1}$; UV(EtOH) $\lambda_{max}(\epsilon)$ 211.5 (40482), 253.0 (25934), 282.0 (21954) and 341.0 (7792) nm; FDMS(DMSO) m/e=362, 364 (M$^+$).

Analysis of C$_{16}$H$_{15}$ClN$_4$O$_2$S:
Theory: C, 52.96; H, 4.17; N, 15.44.
Found: C, 52.84; H, 4.05; N, 15.46.

EXAMPLE 10

Preparation of
N-(7-chloro-2-quinoxalinyl)-2,3-dihydro-
1-methyl-1H-indole-5-sulfonamide In a manner similar to Example 2, N-methylindoline-5-sulfonamide (2.1 g, 10 mmol), sodium hydride (60%, 1.6 g, 40 mmol) and 2,7-dichloroquinoxaline (2.6 g, 13 mmol) were stirred at room temperature overnight. The reaction mixture was worked up as in Example 9 to give the product, (1.9 g, 51%).

Analysis of the title compound gave the following results: mp=213°–214° C.; $^1$H NMR (300 MHz, d$_6$-DMSO) δ2.73(s, 3H, CH$_3$), 2.92(t, 2H, J=8.5 Hz, CH$_2$), 3.40(t, 2H, J=8.5 Hz, CH$_2$ ), 6.48 ( d, 1H, J=8.4 Hz, Ar-H), 7.56–7.80 (m, 4H, Ar-H),7.91(d, 1H, J=8.4 Hz, Ar-H), 8.51(s, 1H, Ar-H), 11.75 (s, 1H, exchanges with D$_2$O, NH); IR KBr: 1608, 1517, 1395, 1152 and 1061 cm$^{-1}$; UV(EtOH) $\lambda_{max}(\epsilon)$ 209.5 (44958), 253.5 (24836) and 290.5 (17570) nm; FDMS (DMSO) m/e=374,376 (M$^+$).

Analysis of C$_{17}$H$_{15}$ClN$_4$O$_2$S:
Theory: C, 54.47; H, 4.03; N, 14.95.
Found: C, 54.25; H, 4.01; N, 14.82.

EXAMPLE 11

Preparation of
4-N',N'-dimethylamino-N-(8-chloro-2-
quinoxalinyl)benzenesulfonamide In a manner similar to Example 2, p-dimethylaminobenzenesulfonamide (400 mg, 2.0 mmol), sodium hydride (60%, 240 mg, 6.0 mmol) and 2,8-dichloroquinoxaline (439 mg, 2.2 mmol) after silica gel flash chromatography (EtOAc/hexane/THF), provided the title compound (325 mg, 45%) as a solid.

Analysis of the title compound gave the following results: $^1$H NMR (300 MHz, d$_6$-DMSO) δ2.93 ( s, 6H, CH$_3$), 6.70(d, 2H, J=9.0 Hz, Ar-H), 7.55( t, 1H, J=8.0 Hz, Ar-H), 7.87 (d, 2H, J=8.0 Hz, Ar-H), 7.99 (d, 2H, J=8.9 Hz, Ar-H), 8.52 (s, 1H, Ar-H), 11.79(s, 1H, exchanges with D$_2$O, NH); IR(KBr) 1599, 1576, 1516, 1445, 1333, 1253, 1184 and 1155 cm$^{-1}$; FDMS(DMSO) m/e=362, 364 (M$^+$).

Analysis of C$_{16}$H$_{15}$ClN$_4$O$_2$S:
Theory: C, 52.96; H, 4.17; N, 15.44.
Found: C, 52.73; H, 4.17; N, 15.20.

Preparation 8

Preparation of 2,5,6- and 2,7,8-trichloroquinoxaline

These intermediates were prepared essentially using the methodology demonstrated in L. McQuaid, et al., supra; U.S. Pat. No. 5,153,196; and U.S. Pat. No. 5,196,421. In this procedure 1,2-diamino-3,4-dichlorobenzene was converted into a mixture of 2,5,6-trichloroquinoxaline and 2,7,8-trichloroquinoxaline by first preparing the 2-hydroxydichloroquinoxaline analogs. This mixture was separated by silica gel flash chromatography (ether/hexanes).

Analysis of the compounds gave the following results:

2,5,6-trichloroquinoxaline: mp=167°–169° C.; $^1$H NMR (300 MHz, $d_6$-DMSO) δ8.0 (d, 1H, J=9.1 Hz, Ar-H), 8.08 (d, 1H, J=9.1 Hz, Ar-H), 9.11(s, 1H, Ar-H); IR(CHCl$_3$) 3011, 1596, 1554, 1467, 1431, 1330, 1256, 1131 and 1106 cm$^{-1}$; UV(EtOH) $\lambda_{max}$(ε) 208.5 (35088), 251.0 (36067) and 329.5 (5626) nm; FDMS(DMSO) m/e=232, 234, 236 (M$^+$).

Analysis of $C_8H_3Cl_3N_2$:

Theory: C, 41.15; H, 1.29; N, 12.00.

Found: C, 41.40; H, 1.40; N, 12.00.

2,7,8-trichloroquinoxaline: mp=118°–119° C; $^1$H NMR (300 MHz, $d_6$-DMSO ) δ8.07 (d, 1H, J=9.1 Hz, Ar-H), 8.12 (d, 1H, J=9.3 Hz, Ar-H), 9.07(s, 1H, Ar-H); IR(CHCl$_3$) 3009, 1592, 1557, 1545, 1475, 1253 and 1113 cm$^{-1}$; FDMS (DMSO) m/e=232, 234, 236 (M$^+$).

Analysis of $C_8H_3Cl_3N_2$:

Theory: C, 41.15; H, 1.29; N, 12.00.

Found: C, 41.15; H, 1.32; N, 12.07.

EXAMPLE 12

Preparation of
4-N',N'-dimethylamino-N-(5,6-dichloro-
2-quinoxalinyl)benzenesulfonamide In a manner similar to Example 2, p-dimethylaminobenzenesulfonamide (200 mg, 1.0 mmol), sodium hydride (60%, 200 mg, 5.0 mmol) and 2,5,6-trichloroquinoxaline (350 mg, 1.5 mmol) were reacted at room temperature overnight. The reaction mixture was worked up as in Example 5, and the dried precipitate was purified by silica gel flash chromatography (MeOH/CH$_2$Cl$_2$) followed by silica gel plate (2 mm, 5% MeOH/CH$_2$Cl$_2$) to yield the title product (183 mg, 46%) as a solid.

Analysis of the title compound gave the following results:
$^1$H NMR (300 MHz, $d_6$-DMSO) δ2.93(s, 6H, CH$_3$), 6.70 (d, 2H, J=9.2 Hz, Ar-H), 7.75 d, 1H, J=8.9 Hz, Ar-H), 7.84–7.91 (overlapping multiplets, 3H, Ar-H), 8.61 (s, 1H, Ar-H), 11.84(s, 1H, exchanges with D$_2$O, NH); IR(KBr) 1595, 1518, 1490, 1323, 1277 and 1152 cm$^{-1}$; FDMS(DMSO) m/e=396, 398, 400 (M$^+$).

Analysis of $C_{16}H_{14}Cl_2N_4O_2S$:

Theory: C, 48.37; H, 3.55; N, 14.10.

Found: C, 48.43; H, 3.56; N, 13.87.

EXAMPLE 13

Preparation of N-(5,6-dichloro-2-quinoxalinyl)-2,3-dihydrobenzofuran-5-sulfonamide In a manner similar to Example 2, 2,3-dihydrobenzofuran-5-sulfonamide (200 mg, 1.0 mmol), sodium hydride (60%, 200 mg, 5.0 mmol) and 2,5,6-trichloroquinoxaline (350 mg, 1.5 mmol) were reacted at room temperature overnight. The reaction mixture was worked up as in Example 5, and the dried precipitate was combined with 140 mg of crude product obtained from a reaction run on the same scale. The combined materials were purified by silica gel flash chromatography (MeOH/CH$_2$Cl$_2$), silica gel plate chromatography (2 mm, 5% MeOH/CH$_2$Cl$_2$) and silica gel flash chromatography (MeOH/CH$_2$Cl$_2$) to provide, after vacuum drying at 80° C., the title product (56 mg, 7%) as a solvate.

Analysis of the title compound gave the following results:
$^1$H NMR (300 MHz, $d_6$-DMSO) δ3.21(t, 2H, J=8.8 Hz, CH$_2$), 4.58(t, 2H, J=8.8 Hz, CH$_2$), 5.73(s, 0.5 H, residual CH$_2$Cl$_2$), 6.89(d, 1H, J=8.4 Hz, Ar-H), 7.77(d, 1H, J=9.0 Hz, Ar-H), 7.88-7.94(overlapping multiplets, 3H, Ar-H), 8.63 (s, 1H, Ar-H), 12.06(s, 1H, exchanges with D$_2$O, NH); IR(KBr) 3232, 1484, 1465, 1342, 1280, 1245 and 1142 cm$^{-1}$; FDMS(DMSO) m/e=395, 397, 399 (M$^+$).

Analysis of $C_{16}H_{11}Cl_2N_3O_3S$ •0.30 CH$_2$Cl$_2$:

Theory: C, 46.42; H, 2.77; N, 9.96.

Found: C, 46.26; H, 2.84; N, 9.84.

EXAMPLE 14

Preparation of
4-N',N'-dimethylamino-N-(7,8-dichloro-
2-quinoxalinyl)benzenesulfonamide In a manner similar to Example 12, p-dimethylaminobenzenesulfonamide (200 mg, 1.0 mmol), sodium hydride (60%, 200 mg, 5.0 retool) and 2,7,8-trichloroquinoxaline. (350 mg, 1.5 mmol) provided the title product (163 mg, 41%) as a solid.

Analysis of the title compound gave the following results:
$^1$H NMR (300 MHz, $d_6$-DMSO) δ2.93(s, 6H, CH$_3$), 6.72(d, 2H, J=9.1 Hz, Ar-H), 7.73(d, 1H, J= 8.9Hz, Ar-H), 7.85 (d, 1H, J=8.9 Hz, Ar-H), 7.99 (d, 2H, J=9.1 Hz, Ar-H), 8.50 (s, 1H, Ar-H), 11.90(s, 1H, exchanges with D$_2$O, NH); IR(KBr) 1597, 1577, 1489, 1456, 1374, 1337, 1323 and 1150 cm$^{-1}$; FDMS(DMSO) m/e=396, 398, 400 (M$^+$).

Analysis of $C_{16}H_{14}Cl_2N_4O_2S$:

Theory: C, 48.37; H, 3.55; N, 14.10.

Found: C, 48.32; H, 3.45; N, 13.92.

EXAMPLE 15

Preparation of N-(7,8-dichloro-2-quinoxalinyl)-2,3-dihydrobenzofuran-5-sulfonamide In a manner similar to Example 12, 2,3-dihydrobenzofuran-5-sulfonamide (200 mg, 1.0 mmol), Sodium hydride (60%, 200 mg, 5.0 mmol) and 2,7,8-trichloroquinoxaline (350 mg, 1.5 mmol) were reacted at room temperature overnight. The reaction mixture was worked up as in Example 5, and the dried precipitate was purified by silica gel flash chromatography (MeOH/CH$_2$Cl$_2$). The resulting solid was triturated with MeOH/CHCl$_3$ (2/1) to provide, after vacuum drying at 65° C., the title product (227 mg, 57%) as a solid.

Analysis of the title compound gave the following results:
$^1$H NMR (300 MHz, $d_6$-DMSO) δ3.22 (t, 2H, J=8.8 Hz, CH$_2$), 4.59(t, 2H, J=8.8 Hz, CH$_2$), 6.90 (d, 1H, J=8.5 Hz, Ar-H), 7.77(d, 1H, J=8.9 Hz, Ar-H), 7.88(d, 1H, J=8.9 Hz, Ar-H), 7.97(dd, 1H, J=1.8, 8.4 Hz, Ar-H), 8.13(s, 1H, Ar-H), 8.51(s, 1H, Ar-H), 12.11(s, 1H, exchanges with D$_2$O, NH); IR(KBr) 1579, 1490, 1452, 1324, 1252 and 1143 cm$^{-1}$; FDMS(DMSO) m/e=395, 397, 399 (M$^+$).

Analysis of $C_{16}H_{11}Cl_2N_3O_3S$:

Theory: C, 48.50; H, 2.80; N, 10.60.

Found: C, 48.77; H, 2.89; N, 10.63.

The compounds of Formula I have been shown to be active against human tumors in vitro. The in vitro data were obtained using CCRF-CEM cells, a human leukemia cell line. Foley et al., *Cancer,* 18:522 (1965). These cells were grown in albumin-free UltraCHO® media (BioWhittaker, Inc., Walkersville, Md.) using standard techniques. See, e.g., G. B. Grindey, et al., *Journal of Molecular Pharmacology*, 16:601 (1979). Dose-response curves were generated for various compounds to determine the concentration required for 50% inhibition of growth ($IC_{50}$). Cluster plates were prepared in duplicate with the compound at various concentrations. Test compounds were dissolved initially in DMSO at a concentration of 4 mg/ml and further diluted with solvent to the desired concentration. Cells in serum-free UltraCHO media were added to the well at a final concentration of $4.8 \times 10^4$ cells/well in a total volume of 2.0 ml. After 72 hours of incubation (95% air, 5% $CO_2$), cell numbers were determined on a ZBI Coulter counter. Cell number for indicated controls at the end of incubation was usually $(4-6) \times 10^5$ cells/well. Cell viability was also measured by staining with 3-[4,5-dimethylthiazol-2-yl]-2,5-diphenyl-tetrazolium bromide (MTT) using standard techniques. R. I. Freshney, *Culture of Animal Cells: A Manual of Basic Technique*, 253–254 (2d ed. 1987).

Table I, infra, shows the results of one such in vitro screening panel. Column 1 refers to the example number of the compound tested; Column 2 depicts the in vitro cytotoxicity against CCRF-CEM cells by relating the concentration of the test compound required for 50% inhibition of growth ($IC_{50}$) of the cells in the well. The designation "CSQ" refers to the compound 4-amino-N-(5-chloro-2-quinoxalinyl)benzenesulfonamide and is used as a comparator.

TABLE I

Activity of the Compounds of Formula I Against Tumor Cells In Vitro

| Example Number | (CCRF-CEM) $IC_{50}$ µg/ml |
|---|---|
| CSQ | 0.8 |
| 1 | 0.8 |
| 2 | 0.1 |
| 3 | 0.3 |
| 4 | 0.3 |
| 5 | 0.2 |
| 6 | 0.4 |
| 7 | 1.2 |
| 8 | 1.5 |
| 9 | 10.4 |
| 10 | 10.8 |
| 11 | 15.1 |
| 12 | 7.2 |
| 13 | 6.0 |
| 14 | 4.6 |
| 15 | 10.8 |

Since the compounds of Formula I are antineoplastic agents, the invention also provides a method of treating a susceptible neoplasm in a mammal which comprises administering to a mammal in need of said treatment an effective amount of a compound of Formula I or a pharmaceutically acceptable salt or solvate thereof. In particular, the present compound is useful in treating solid tumors including carcinomas such as ovarian, non-small cell lung, gastric, pancreatic, prostate, renal cell, breast, colorectal, small cell lung, melanoma, and head and neck; and sarcomas such as Kaposi's sarcoma and rhabdomyosarcoma.

The compounds of Formula I are usually administered in the form of pharmaceutical compositions. These compounds can be administered by a variety of routes including oral, rectal, transdermal, subcutaneous, intravenous, intramuscular, and intranasal. Such compositions are prepared in a manner well known in the pharmaceutical art and comprise at least one active compound.

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

For those formulations in which a soluble form of a compound of Formula I is necessary, such as an intravenous formulation, it is frequently necessary to formulate the compound of Formula I with a basic amine such as N-methylglucamine (also known as meglumine) in order to solubilize the compound. Neutralization of such solutions with dilute acids will usually result in the formation of a large amount of precipitate.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| N-(7-chloro-2-quinoxalinyl)-2,3-dihydro-1-methyl-1H-indole-5-sulfonamide | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| 4-N',N'-dimethylamino-N-[(5-chloro-2-quinoxalinyl)-3-chlorobenzenesulfonamide | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| N-(5-chloro-2-quinoxalinyl)-2,3-dihydro-1H-indene-5-sulfonamide | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| N-(5,7-dichloro-2-quinoxalinyl)-2,3-dihydrobenzofuran-5-sulfonamide | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh. U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
| --- | --- |
| N-(7,8-dichloro-2-quinoxalinyl)-benzofuran-5-sulfonamide | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 225 mg of active ingredient are made as follows:

| Ingredient | Amount |
| --- | --- |
| N-(5-chloro-2-quinoxalinyl)-benzo[B]thiophene-3-sulfonamide | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| N-(6-methyl-2-quinoxalinyl)-1H-indole-6-sulfonamide | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| 4-N',N'-dimethylamino-N-[(5,6-diiodo-2-quinoxalinyl)-5-fluoro-3-methyl-benzenesulfonamide | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
| --- | --- |
| 4-N',N'-dimethylamino-N-(7,8-dichloro-2-quinoxalinyl)-naphthalenesulfonamide | 250.0 mg |
| N-methylglucamine | 375.0 mg |
| Isotonic saline | 1000 ml |

Formulation Example 10

A topical formulation may be prepared as follows:

| Ingredient | Quantity |
| --- | --- |
| N-(5,6-difluoro-2-quinoxalinyl)-1-methyl-1H-indole-6-sulfonamide | 1–10 g |
| Emulsifying Wax | 30 g |
| Liquid Paraffin | 20 g |
| White Soft Paraffin to | 100 g |

The white soft paraffin is heated until molten. The liquid praffin and emulsifying wax are incorporated and stirred until dissolved. The active ingredient is added and stirring is continued until dispersed. The mixture is then cooled until solid.

Other preferred formulations employed in the methods of the present invention utilize transdermal delivery devices ("patches"). Such transdermal patches may be used to provide continuous or discontinuous infusion of the compounds of the present invention in controlled amounts. The construction and use of transdermal patches for the delivery of pharmaceutical agents are well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

We claim:
1. A compound of the formula

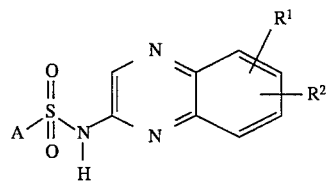

wherein:

A is naphthyl, benzofuryl, 2,3-dihydrobenzofuryl, benzothienyl, indolyl, N-methyl indolyl, indolinyl, N-methyl indolinyl indanyl, or indenyl, said groups being optionally substituted with one or more halo, trifluoromethyl, $C_1$–$C_6$ alkyl, or —$NR^3R^4$, where $R^3$ and $R^4$ are independently selected from the group consisting of hydrogen and $C_1$–$C_6$ alkyl;

$R^1$ and $R^2$ are independently selected from the group consisting of hydrogen, trifluoromethyl, halo, and $C_1$–$C_6$ alkyl, provided that $R^1$ and $R^2$ cannot both be hydrogen; provided that when one of $R^1$ and $R^2$ is hydrogen and the other is halo or methyl, $R^3$ and $R^4$ cannot both be hydrogen; or a tautomer or pharmaceutically acceptable salt or solvate thereof.

2. A compound as claimed in claim 1 wherein at least one of $R^1$ and $R^2$ is halo or a tautomer or pharmaceutically acceptable salt or solvate of said compound.

3. A compound of as claimed in claim 2 wherein at least one of $R^1$ and $R^2$ is chloro or a tautomer or pharmaceutically acceptable salt or solvate of said compound.

4. A compound as claimed in claim 3 wherein A is indolinyl, indolyl, benzofuryl, benzothienyl, 2,3-dihydrobenzofuryl, indenyl, or indanyl, said groups being optionally substituted with one, two, or three moieties selected from the group consisting of methyl, ethyl, chloro, trifluoromethyl, and —$NR^3R^4$ or a tautomer or pharmaceutically acceptable salt or solvate of said compound.

5. A compound as claimed in claim 4 which is N-(5-chloro-2-quinoxalinyl)-2,3-dihydro-1-methyl-1H-indole-5-sulfonamide, N-(5-chloro-2-quinoxalinyl)-2,3-dihydrobenzofuran-5-sulfonamide, N-(5-chloro-2-quinoxalinyl)-benzofuran-5-sulfonamide, N-(5-chloro-2-quinoxalinyl)-1-methyl-1H-indole-5-sulfonamide, N-(6-chloro-2-quinoxalinyl)-2,3-dihydro-1-methyl-1H-indole-5-sulfonamide, or N-(7-chloro-2-quinoxalinyl)-2,3-dihydro-1-methyl-1H-indole-5-sulfonamide, or a tautomer or pharmaceutically acceptable salt or solvate thereof.

6. A compound as claimed in claim 4 wherein one of $R^1$ and $R^2$ is chloro and the other is halo or a tautomer or pharmaceutically acceptable salt or solvate of said compound.

7. A compound as claimed in claim 6 wherein at least one of $R^1$ and $R^2$ is chloro or a tautomer or pharmaceutically acceptable salt or solvate of said compound.

8. A compound as claimed in claim 7 which is N-(5,6-dichloro-2-quinoxalinyl)-2,3-dihydrobenzofuran-5-sulfonamide, or N-(7,8-dichloro-2-quinoxalinyl)-2,3-dihydrobenzofuran-5-sulfonamide, or a tautomer or pharmaceutically acceptable salt or solvate thereof.

9. A pharmaceutical formulation comprising an effective amount of a compound of the formula

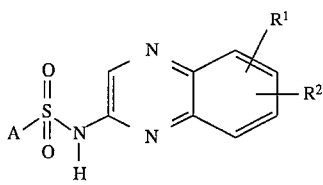

wherein:

A is naphthyl, benzofuryl, 2,3-dihydrobenzofuryl, benzothienyl, indoly, N-methyl indolyl, indolinyl, N-methyl indolinyl indanyl, or indenyl, said groups being optionally substituted with one or more halo, trifluoromethyl, $C_1$–$C_6$ alkyl, or —$NR^3R^4$, where $R^3$ and $R^4$ are independently selected from the group consisting of hydrogen and $C_1$–$C_6$ alkyl;

$R^1$ and $R^2$ are independently selected from the group consisting of hydrogen, trifluoromethyl, halo, and $C_1$–$C_6$ alkyl, provided that $R^1$ and $R^2$ cannot both be hydrogen; provided that when one of $R^1$ and $R^2$ is hydrogen and the other is halo or methyl, $R^3$ and $R^4$ cannot both be hydrogen; or a tautomer or pharmaceutically acceptable salt or solvate thereof, in combination with one or more pharmaceutically acceptable carriers, diluents, or excipients.

10. A formulation as claimed in claim 9 employing a compound wherein at least one of $R^1$ and $R^2$ is halo or a tautomer or pharmaceutically acceptable salt or solvate of said compound.

11. A formulation as claimed in claim 10 employing a compound wherein at least one of $R^1$ and $R^2$ is chloro or a tautomer or pharmaceutically acceptable salt or solvate of said compound.

12. A formulation as claimed in claim 11 employing a compound wherein A is indolinyl, indolyl, benzofuryl, benzothienyl, 2,3-dihydrobenzofurtyl, indenyl, or indanyl, said groups being optionally substituted with one, two, or three moieties selected from the group consisting of methyl, ethyl, chloro, trifluoromethyl, and —$NR^3R^4$, or a tautomer or pharmaceutically acceptable salt or solvate of said compound.

13. A formulation as claimed in claim 12 employing a compound which is N-(5-chloro-2-quinoxalinyl)-2,3-dihydro-1-methyl-1H-indole-5-sulfonamide, N-(5-chloro-2-quinoxalinyl)-2,3-dihydrobenzofuran-5-sulfonamide, N-(5-chloro-2-quinoxalinyl)-benzofuran-5-sulfonamide, N-(5-chloro-2-quinoxalinyl)-1-methyl-1H-indole-5-sulfonamide, N-(6-chloro-2-quinoxalinyl)-2,3-dihydro-1-methyl-1H-indole5-sulfonamide, or N-(7-chloro-2-quinoxalinyl)-2,3-dihydro-1-methyl-1H-indole-5-sulfonamide, or a tautomer or pharmaceutically acceptable salt or solvate thereof.

14. A formulation as claimed in claim 12 employing a compound wherein one of $R^1$ and $R^2$ is chloro and the other is halo or a tautomer or pharmaceutically acceptable salt or solvate of said compound.

15. A formulation as claimed in claim 14 employing a compound which is N-(5,6-dichloro-2-quinoxalinyl)-2,3-dihydrobenzofuran-5-sulfonamide, or N-(7,8-dichloro-2-quinoxalinyl)-2,3-dihydrobenzofuran-5-sulfonamide, or a tautomer or pharmaceutically acceptable salt or solvate thereof.

* * * * *